US011832977B2

(12) United States Patent
Maur et al.

(10) Patent No.: US 11,832,977 B2
(45) Date of Patent: Dec. 5, 2023

(54) METHOD AND APPARATUS FOR GENERATING A 2D PANORAMIC IMAGE

(71) Applicants: DENTSPLY SIRONA inc., York, PA (US); SIRONA DENTAL SYSTEMS GMBH, Bensheim (DE)

(72) Inventors: Susanne Maur, Bensheim (DE); Stefan Eichner, Heidelberg (DE)

(73) Assignee: DENTSPLY SIRONA INC., York, PA (US)

( * ) Notice: Subject to any disclaimer, the term of this patent is extended or adjusted under 35 U.S.C. 154(b) by 377 days.

(21) Appl. No.: 17/424,951

(22) PCT Filed: Jan. 23, 2020

(86) PCT No.: PCT/EP2020/051649
§ 371 (c)(1),
(2) Date: Jul. 22, 2021

(87) PCT Pub. No.: WO2020/152278
PCT Pub. Date: Jul. 30, 2020

(65) Prior Publication Data
US 2022/0022827 A1   Jan. 27, 2022

(30) Foreign Application Priority Data

Jan. 23, 2019 (EP) .................................... 19153361

(51) Int. Cl.
*A61B 6/14*  (2006.01)
*G06T 7/73*  (2017.01)
(Continued)

(52) U.S. Cl.
CPC .............. *A61B 6/14* (2013.01); *A61B 6/5241* (2013.01); *G06T 3/4038* (2013.01); *G06T 7/74* (2017.01);
(Continued)

(58) Field of Classification Search
CPC ........... A61B 6/14; A61B 6/5241; G06T 7/74; G06T 3/4038; G06T 2207/10116; G06T 2207/30036
See application file for complete search history.

(56) References Cited

FOREIGN PATENT DOCUMENTS

JP    2010148676 A  *  7/2010
JP    2016007338 A  *  1/2016

* cited by examiner

*Primary Examiner* — David P Porta
*Assistant Examiner* — Fani Polyzos Boosalis
(74) *Attorney, Agent, or Firm* — DENTSPLY SIRONA INC.

(57) ABSTRACT

The present invention proposes a method for producing a 2D panoramic image of an oral cavity comprising the steps: A) provision of a plurality of projection images acquired during an at least partial revolution of a recording unit comprising a radiation source and an electronic image sensor about the oral cavity in a given position; B) calculation of an image including at least one anatomical feature from the plurality of projection images using a calculation rule with reconstruction parameters; C) provision of a model of the at least one anatomical feature, which describes the at least one anatomical feature in a target position in an image; D) identification of the at least one anatomical feature in the calculated image; E) determination of a deviation between an actual position of the at least one identified anatomical feature in the calculated image and the target position of the at least one anatomical feature in the model by applying a metric; F) variation of at least one of the reconstruction parameters and recalculation of at least one part of the image that shows the at least one anatomical feature using the calculation rule and the at least partially varied reconstruction parameters or variation of a pixel transformation and application of the pixel transformation to at least one part of the calculated image that shows the at least one anatomical (Continued)

feature, so that at least this part of the image is recalculated; G) derivation of the 2D panoramic image from the recalculated image; and H) outputting the 2D panoramic image.

15 Claims, 7 Drawing Sheets

(51) Int. Cl.
*A61B 6/00* (2006.01)
*G06T 3/40* (2006.01)
(52) U.S. Cl.
CPC ............... *G06T 2207/10116* (2013.01); *G06T 2207/30036* (2013.01)

a)

b)

c)

a)  b)

METHOD AND APPARATUS FOR GENERATING A 2D PANORAMIC IMAGE

CROSS-REFERENCE TO RELATED APPLICATIONS

This is a National Phase application of International Application No. PCT/EP2020/051649 filed Jan. 23, 2020, which claims the benefit of and priority to European Patent Application Number 19153361.1 filed on 23 Jan. 2019 which are herein incorporated by reference for all purposes.

TECHNICAL FIELD

The present invention relates to a method for generating a 2D panoramic image of an oral cavity comprising the following steps
  A) Provision of a plurality of projection images acquired during an at least partial revolution of a recording unit comprising a radiation source and an electronic image sensor about the oral cavity in a given position, and
  B) Calculation of an image including at least one anatomical feature from the plurality of projection images using a calculation rule with reconstruction parameters.

The present invention further relates to an apparatus for producing a 2D panoramic image of an oral cavity, which comprises a recording unit having a radiation source and an electronic image sensor, and a computer which is operatively connected to the recording unit. The computer is configured to carry out the method according to the invention.

BACKGROUND

In the field of dental diagnostic radiology, it is often necessary to produce X-ray images of the entire oral cavity including the jaw bones and the teeth embedded therein. For this purpose, the head of the patient including the oral cavity is arranged in such a way that a recording unit comprising a radiation source and an electronic image sensor can revolve around said head of the patient, thus acquiring a plurality of projection images of the dental arches of the lower and/or upper jaw at a plurality of angles. If the acquisition is carried out using an electronic image sensor comprising a matrix-like arrangement of pixels, a 2D panoramic image can be calculated from this plurality of recorded projection images. This 2D panoramic image then sharply depicts a selected, curved slice of the dental arch in a two-dimensional developed view.

The calculation of the 2D panoramic image from the plurality of projection images follows a calculation rule or algorithm that uses reconstruction parameters. On one hand, the reconstruction parameters describe the geometric mapping of each individual projection, i.e. the recording geometry. Imaging properties of the 2D panoramic image to be calculated that are selected by a user, or even automatically, during the calculation of the 2D panoramic Image can furthermore be defined and optionally also changed via the reconstruction parameters. One example of this is the automatic selection of the curved slice within the dental arch that is sharply represented in the 2D panoramic image. The initial imaging properties are thereby defined under the assumption that the oral cavity is located in a target position In practice, however, this is often not the case. Despite well-trained personnel, more or less significant deviations between the desired target position of the oral cavity and the actually implemented given position continue to occur. The patient may also move during the recording, so that the difference between the given position during the acquisition of a projection and the target position can change from projection to projection as well.

It has been shown that, among other things, a diagnostic assessment of a 2D panoramic image also depends on what the position and orientation of the oral cavity relative to the radiation source or the image sensor was during the revolution of the recording unit about the oral cavity. In a 2D panoramic image of an oral cavity that is mispositioned with respect to an ideal position and orientation, it may not be possible to distinguish pathological features of the dentition from features of the 2D panoramic image caused by the mispositioning. Deviations from an ideal position and orientation can therefore lead to a situation in which a diagnosis based on the calculated 2D panoramic image is not possible; or possible only for very experienced diagnosticians.

In contrast, compared to presentations of a mispositioned oral cavity in a 2D panoramic image, the object of the present invention is to provide a method that facilitates diagnosis. A further object of the present invention is to provide a method that facilitates diagnosis, independent of the position and orientation of the oral cavity relative to the recording unit during the acquisition of the projection images.

SUMMARY

At least one of the aforementioned objects is achieved by a method for generating a 2D panoramic image of an oral cavity, which comprises the steps:
  A) Provision of a plurality of projection images acquired during an at least partial revolution of a recording unit comprising a radiation source and an electronic image sensor about the oral cavity in a given position.
  B) calculation of an image including at least one anatomical feature from the plurality of projection images using a calculation rule with reconstruction parameters,
  C) provision of a model of the at least one anatomical feature, which describes the at least one anatomical feature in a target position in an image,
  D) identification of the at least one anatomical feature in the calculated image,
  E) determination of a deviation between an actual position of the at least one Identified anatomical feature in the calculated image and the target position of the at least one anatomical feature in the model by applying a metric,
  F) variation of at least one of the reconstruction parameters and recalculation of at least one part of the image that shows the at least one anatomical feature using the calculation rule and the at least partially varied reconstruction parameters or application of a pixel transformation to at least one part of the calculated image that shows the at least one anatomical feature, so that at least this part of the image is recalculated,
  G) Derivation of the 2D panoramic image from the recalculated image, and
  H) Outputting the 2D panoramic image.

The provision of the plurality of projection images is initially understood only to mean that the projection images are delivered in the form of data for further processing, for example to a computer which implements the method according to the invention.

In one embodiment, however, the provision of the plurality of projection images comprises an acquisition of said plurality of projection images during an at least partial revolution of the recording unit about the oral cavity.

It goes without saying that, at least in one embodiment of the invention, the radiation source produces X-ray radiation during the operation of the recording unit and the image sensor is a sensor for said X-ray radiation.

Such an electronic image sensor can comprise a CCD or CMOS detector, for example, wherein, in a scintillation layer in front of the CCD or CMOS detector, the X-ray radiation is converted into electromagnetic radiation in a wavelength range to which the detector is sensitive. On the other hand, such an electronic image sensor can also be a direct conversion detector, in which the X-ray radiation is converted directly into an electrical signal. In one embodiment of the invention, the image sensor is a so-called full frame sensor, in which, at one point in time, all the pixels of the sensor are exposed simultaneously and then read in their entirety. In one embodiment of the invention, the individual pixels of the image sensor are arranged in a matrix-like manner.

During the at least partial of the recording unit comprising the radiation source and the image sensor around the oral cavity, a plurality of projection images depicting the oral cavity in a plurality of radiation penetration directions is produced, and each projection is preferably stored in the form of raw data The actual 2D panoramic image is not generated from the projection images until afterwards and possibly also significantly later than the acquisition of the projection images. A sharp, curved slice of the dental arch, which is also referred to in the present application as a panoramic layer, is mapped mathematically in the plane of the image.

Varying one or more of the reconstruction parameters or applying a pixel transformation in Step F) allows not only the position of the sharp layer, i.e. the image plane that is sharply imaged in the 2D panoramic image, to be selected and changed, but also the position of the oral cavity or individual elements thereof, such as teeth, upper jaw bones and lower jaw bones, depicted in the calculated 2D panoramic image.

In the context of the present application, the given position of the head, i.e. the oral cavity and the elements located therein, is always understood to be the position and orientation of the head relative to the recording unit. On the other hand, the actual position of the anatomical feature refers to the true position of said anatomical feature in the calculated image. The target position refers to the desired position, i.e. the position of the anatomical feature to be achieved in the calculated image.

In principle, it is desirable for all 2D panoramic images to be generated from projection images of the oral cavity with an optimum position of the oral cavity relative to the recording unit. However, since deviations of the true given position from the position of the patient's head, and thus of the oral cavity with the jaw bones, that is ideal for a diagnosis will always occur, the invention proposes changing the position of the at least one anatomical feature and with it the presentation of the entire oral cavity and its elements in the displayed 2D panoramic image, so that the presentation in the displayed 2D panoramic image corresponds to the desired presentation.

To achieve the desired presentation in the 2D panoramic image, an image with at least one anatomical feature is first calculated from the plurality of projection images with reconstruction parameters according to a calculation rule, and a deviation between an actual position of the at least one anatomical feature identified in the image and the target position of the at least one anatomical feature as described by the model is calculated by applying a metric. It goes without saying that this deviation is equivalent to a correlation, which describes the degree of agreement between the anatomical feature in the calculated image and the anatomical feature in the model.

For the present invention it is initially insignificant whether the image calculated in the steps prior to outputting the 2D panoramic image and used for the subsequent calculations is a 2D image, for example a 2D panoramic image, a 3D image, for example a 3D volume, or an abstract image description in the form of image data.

After the determination of the deviation between the actual position of the at least one anatomical feature in the calculated image and the target position of said anatomical feature in the model by applying a metric, the actual position of the at least one anatomical feature in the image is changed.

According to the invention, there are two options for this change to the actual position of the at least one anatomical feature in the calculated image.

The first is that, in one embodiment, at least one of the reconstruction parameters can be varied in order to change the actual position of the at least one anatomical feature in the calculated image, wherein an at least partial recalculation of the image is then carried out according to the calculation rule with the at least partially varied reconstruction parameters.

The second is that, in one embodiment, in order to change the position of the at least one anatomical feature in the calculated image, a pixel transformation can be varied and then applied to at least one part of the calculated image, so that at least this part of the image is recalculated.

While, in the first variant, the image is recalculated from the projection images after a variation of at least one reconstruction parameter, as it were from the beginning, in the second variant the image calculated in Step B) is used as the starting point of the calculation and is changed by applying a local or global pixel transformation.

In one embodiment, such a pixel transformation is a local and/or global image deformation or image distortion, frequently also referred to as image warping. Pixels are in particular interpolated in such a pixel transformation, so that there can be no improvement of the image quality. In return, the application of a pixel transformation leaves the other imaging properties completely untouched.

It goes without saying that, in one embodiment, an initial pixel transformation is predefined, for example an imaging of each pixel onto itself (this would be used if there is no deviation between the actual position and the target position), and is varied as a function of the determined deviation.

The method according to the invention can also be described as a correction of a deviation of the given position of the oral cavity in the projection images, which is determined by the recording geometry, from an optimum target position defined by the model. In each case, the deviation between the actual position in the respectively calculated image and the target position defined by the model is determined on the basis of at least one anatomical feature, which can be identified in the calculated image and is also described by the model.

In one embodiment, it can be sufficient to determine the deviation in Step E), to then, with a single variation of at least one of the reconstruction parameters or with a single variation of the pixel transformation and applying the varied pixel transformation in Step F), results in an image and thus at the 2D panoramic image with an actual position of the anatomical feature, and with it of the oral cavity, in the displayed 2D panoramic image which substantially corresponds to the target position.

In one embodiment of the invention, however, the deviation between the actual position of the at least one anatomical feature in the calculated image and the target position of said anatomical feature in the model is optimized by means of iteration. For this purpose, the method according to the invention in one embodiment comprises the following steps after Step F) and before Step G)

I) Redetermination of the deviation between the actual position of the at least one
identified anatomical feature in the calculated image and the target position of the at least one anatomical feature in the model by applying a metric, J) Repetition of Steps F) and 1) until the determined deviation is less than a specified threshold value and K) If the entire image was not recalculated in Step F), recalculation of at least one part of the image that was not yet recalculated in Step F) using the at least partially varied reconstruction parameters or applying the at least one pixel transformation to at least one part of the image that has not yet been recalculated in Step F).

In the context of the present application, model refers to a description of one or more anatomical features of the head, which, in comparison to a complete image, is abstracted, i.e. simplified. The determination of the metric, which characterizes the deviation between the calculated image and the description of the anatomical feature in the model, is significantly faster than a comparison of two complete images, for example acquired at different times.

In one embodiment of the invention, in addition to the description of the anatomical feature or features, the model can also describe other elements that are, however, not used for determining the deviation.

In one embodiment, the model can in particular be extracted by calculation from a plurality of images respectively based on a plurality of projection images, in particular 2D panoramic images. In another embodiment, the model is based on a definition specified by a user.

In one embodiment, the data volume of the model is smaller than the data volume of the calculated image, preferably the 2D panoramic image. In another embodiment, the model describes the at least one anatomical feature with one first number of pixels, wherein the calculated image, in particular the 2D panoramic image, comprises a second number of pixels, and wherein the first number of pixels can be smaller than the second number of pixels.

In doing so, the model optionally describes the anatomical feature in a 2D description or in a 3D description. If the anatomical feature is described in the model in the form of a 3D description but the calculated Image is a 2D image, in Steps E) and, if applicable. 1) in one embodiment of the method for determining the metric, a 2D description is first calculated from the 3D description, which represents a 2D projection of the at least one anatomical feature, which corresponds to a presentation of the at least one anatomical feature in an ideal 2D panoramic image.

In one embodiment, after the variation of the at least one reconstruction parameter in Step F), the entire image can be recalculated to once more compare the thus calculated image with the model, or only that part of the image which shows the at least one anatomical feature is recalculated. In the second case, at least one part of the image not yet calculated in Step F) is recalculated with the optimized reconstruction parameters only once the at least one reconstruction parameter is optimized such that the metric of the deviation between the actual position of the at least one anatomical feature in the calculated image and the target position specified by the model is optimized.

In Step F), a pixel transformation can similarly be applied either to the complete calculated image, so that the entire image changes, or the pixel transformation can be applied to only that part of the image that shows the at least one anatomical feature. The pixel transformations are not applied to the entire image calculated in Step B), or to at least one part of the image from Step B) not initially subjected to the pixel transformation(s) in Step F), until the metric of the deviation between the actual position of the at least one anatomical feature in the calculated image and the target position specified by the model is optimized.

In one embodiment, the reconstruction parameters of the calculation rule describe both the recording geometries during the acquisition of the projection images and the desired imaging properties of the calculated image.

In one embodiment of the invention, the recording geometry is determined by the radiation source, the image sensor, the oral cavity and the relative arrangement of these elements to one another. In one embodiment of the invention, the imaging properties include the actual position of the anatomical feature and/or the oral cavity in the image, a position of the layer that is sharply imaged in the displayed 2D panoramic image, a radiation penetration angle and a thickness of the layer that is sharply or substantially sharply imaged in the displayed 2D panoramic image. The imaging properties different from the position of the anatomical feature or the oral cavity are also referred to in the context of the present application as further imaging properties.

In one embodiment of the invention, the at least one reconstruction parameter varied in Step F) describes a transformation parameter of a coordinate transformation for the rotation and/or translation of the oral cavity or the head relative to the recording unit.

It goes without saying that suitable procedures for the image analysis and the difference analysis can be used to determine the deviation between the at least one anatomical feature identified in the calculated image in Step D) and the feature in the model. A suitable distance measure, for example the sum of all Euclidean distances between reference points in the calculated image and in the model, can be used as the metric.

The variation of the at least one reconstruction parameter or the application of the pixel transformation in Step F) can be carried out manually by a user or by means of an automated optimization method.

In one embodiment, the optimization of the deviation is performed by using of an optimization method known from the state of the art, for example brute force.

The calculation rule for calculating the image comprises a plurality of reconstruction parameters. In one embodiment, the calculation rule is designed such that the variation of the at least one reconstruction parameter in Step F) leaves at least one further imaging property different from the position of the oral cavity, but preferably all further imaging properties of the respectively calculated image and the 2D panoramic image displayed in Step H) different from the position of the oral cavity, substantially unchanged.

In one embodiment, the at least one further imaging property of the displayed 2D panoramic image that is not affected by the variation of the at least one reconstruction parameter is selected from a position of the layer that is sharply imaged in the 2D panoramic image, a radiation penetration angle and a thickness of the layer that is sharply or substantially sharply imaged in the 2D panoramic layer If a definition of the recording geometry of the individual projection images is known, for example in the form of a system matrix, it is possible to change and optimize the position of the oral cavity and the further imaging properties independently of one another by varying at least one reconstruction parameter, but preferably a plurality of reconstruction parameters. A system matrix permits an interpretation of the data in a 3D space and thus also describes the correlations between the imaging parameters. The assumed position of the oral cavity on which the calculation is based is essentially varied until the difference between the model of the anatomical feature and the presentation of the anatomical feature in the 2D panoramic image to be displayed is minimal. The reconstruction parameters for modifying the position and, if applicable, the at least one further imaging property are changed for each recalculation of the image and can be likewise be determined if the system matrix is known.

In one embodiment, the position of the oral cavity and at least one of the further imaging properties are adjusted or corrected at the same time.

In one embodiment of the invention, the varying of a reconstruction parameter in Step F) leads to a change of not only the assumed position of the oral cavity on which the calculation is based, but at the same time also to a change of at least one further imaging property, for example the position of the sharply depicted layer.

Thus, for example in one embodiment, the radiation penetration angle range of the individual projection images available for the calculation of the individual pixels of the image is a function of both the position of the sharp layer selected for the calculation and the physical recording geometry.

The respective radiation penetration angle on which the calculation of the Individual pixels of the image is based can be varied within the maximum radiation penetration angle, which is locally defined by the recording geometry, as a function of the given data.

The local layer thickness of a pixel of a 2D panoramic image, however, is in turn a function of the radiation penetration angle of the underlying projection images selected for the calculation of this pixel of the 2D panoramic image. The smaller the radiation penetration angle of the projection images selected to calculate a pixel of the 2D panoramic image, the larger the resulting layer thickness in the calculated pixel.

The selection of the position of the sharp layer in the 2D panoramic image thus also indirectly affects the local layer thickness in the respective pixels.

Therefore, in one embodiment, the calculation rule is selected such that, similar to a correction of an image distortion, a change of the at least one reconstruction parameter does not affect substantially any of the further imaging properties.

In one embodiment, the change to the at least one further imaging property is substantially compensated by additionally changing at least one further reconstruction parameter. In other words, the optimization of the reconstruction parameters may result in undesirable changes to a further imaging property. This can be substantially offset by varying reconstruction parameters that have no or almost no impact on the image of the anatomical feature.

In the context of the present application, in addition to very specific anatomical structures, the term anatomical feature also includes image structures or image regions comprising such image structures that can be attributed to the anatomy of the head with the recorded oral cavity, but in which the position, orientation, shape or symmetry of one or more parts of the body cannot specifically be identified as generating the image structure. One example of such an image structure forming an anatomical feature in the context of the present application is the shape of a shading that occurs reproducibly in every image of an oral cavity.

In one embodiment, the term anatomical feature in the context of the present application also includes structures, such as an implant or a crown, that are artificial, but are permanently attached to the human body.

While the anatomical feature in an embodiment can be attributed to an element of the oral cavity, the anatomical feature in one embodiment can also be attributed to an element of the head surrounding the oral cavity or the spine.

In one embodiment of the invention, the anatomical feature is selected from a position and/or orientation and/or a shape and/or a symmetry of a tooth, a temporomandibular joint, a palate, at least one element of the spinal column, for example a vertebra or an intervertebral disc, a collarbone and/or a bone.

In one example, the anatomical feature is the shape of the palate of the oral cavity, wherein, in an optimum position of the oral cavity relative to the recording unit, said palate exhibits a symmetrical shape with a substantially horizontal profile in a 2D panoramic image. On the other hand, a dorsal inclination of the head, for example, results in the palate looking like a gabled roof in the calculated 2D panoramic image.

In one embodiment, the profile of the teeth of the upper jaw and/or the lower jaw serves as an anatomical feature in the context of the present application. With an optimum position of the oral cavity relative to the recording unit, the teeth exhibit a slight smile. In other words, the profile of the teeth of the upper jaw results in a slightly convexly curved shape, and the profile of the teeth of the lower jaw results in a slightly concavely curved shape. On the other hand, a dorsal inclination of the head has the effect that the teeth of the upper jaw have a slightly concave profile, while the teeth of the lower jaw have a slightly convex profile.

The profile of the roots of the front teeth can also be viewed as an anatomical feature. In an optimum position of the oral cavity relative to the recording unit, the roots of the front teeth have a maximum inclination with respect to a perpendicular parallel to the axis of rotation of the recording unit.

Bone structures in particular are frequently right/left symmetrically positioned in the head. In a 2D panoramic image of an optimally positioned oral cavity, the bone structures of the head are symmetrically imaged as well. This knowledge can be incorporated into the anatomical model, and used to identify the reconstruction parameter optimized with respect to the position or a pixel transformation that optimizes the position. Examples of such symmetrical bone structures in an optimum position of the head, and thus of the oral cavity, are the temporomandibular joints, the jaw bone, the palatal bones and the eye sockets. The position of the vertebral bodies allows inferences about the position of the oral cavity to be made as well.

In an optimum position of the oral cavity, the projection of the temporomandibular joints, for example, should be horizontally symmetrical in the panoramic image. The position and size of the image of the temporomandibular joints allows inferences to be made about the position of the head or oral cavity.

In one embodiment of the method according to the invention, in Step D), at least one anatomical feature is identified in a first section and at least one anatomical feature is identified in a second section of the calculated image.

in Step E), a deviation between the at least one anatomical feature identified in the first section and the model of the at least one anatomical feature is determined by applying a metric and a deviation between the at least one anatomical feature identified in the second section and the model of the at least one anatomical feature is determined by applying a metric, in Step F), at least one reconstruction parameter for the first section and at least one reconstruction parameter for the second section of the calculated image are varied separately from one another.

in Step 1), a deviation between the at least one identified anatomical feature in the first section and the model is again determined by applying a metric, and a deviation between the at least one identified anatomical feature in the second section and the model is again determined by applying a metric, and in Step J), Steps F) and 1) are repeated until the respective determined deviations are less than a specified threshold value.

The same reconstruction parameters, or partially or completely different reconstruction parameters, can be varied for the first section and the second section.

Among other things, such an embodiment is suitable for correcting a change in the position of the oral cavity during a revolution of the recording unit, so that the displayed 2D panoramic image looks as if the underlying projection images were acquired using a single, optimized and stationary position of the oral cavity. In such an embodiment, the first section and the second section of the calculated image then lie directly or indirectly adjacent to one another in the direction of the profile of the dental arch or in the direction of the revolution of the recording unit, i.e. in the direction of the horizontal profile of the dental arch, so that the first and the second section correspond to different points in time during the acquisition of the respective underlying projection images. It goes without saying that such an embodiment is not limited to two sections, but is in particular suitable for a plurality of sections. Such an embodiment is in particular not limited to a first and a second section that are directly adjacent to one another.

The at least one reconstruction parameter is respectively varied for the individual sections of the panoramic image, until the metric of the deviation between the actual position of the anatomical feature in the first section of the calculated image and the target position of the feature in the model and the metric of the deviation between the actual position of the anatomical feature in the second section of the calculated image and that of the feature in the model are optimized.

In another embodiment of the invention, the first section of the calculated image is an upper section, which includes at least one part of the upper jaw, and the second section of the calculated image is a lower section, which includes at least one part of the lower jaw. Different positions of the upper jaw and the lower jaw due to the bite can thus be corrected independently of one another. It is furthermore possible to correct movements of the lower jaw relative to the upper jaw during the acquisition of the projection images independently of one another.

In one embodiment, the upper section includes the entire upper jaw and the lower section includes the entire lower jaw.

The object of the method according to the invention is to take mispositionings of the head of the patient during the acquisition of the projection images into account by using an optimized calculation of the 2D panoramic image be displayed, to thus obtain 2D panoramic images that facilitate diagnosis. In particular the comparison with panoramic layer images, which are based on acquisitions of projection images that take place in advance or afterwards, is facilitated.

The described correction of the position during the calculation of the panoramic layer image can, however, also have local and/or global negative effects on the image quality. In the first variant of the correction, this is due to the fact that the radiation source and the image sensor in the acquisition of the projection images are adjusted to a target position of the oral cavity, and any deviation from the target position results in a deterioration of the image quality. In the case of only small deviations, however, this is barely noticeable. But, if the deviations become too large, the image quality decreases significantly. In the second variant, a potential deterioration of the local image quality is a result of the pixel transformation.

There is the additional risk that the user will no longer take adequate care to position the patient properly, because he relies on the correction of the presentation of the 2D panoramic image displayed with the method according to the invention. Since the image quality is still good with smaller deviations, the user also does not know that the positioning was not optimum. Ever more complex and larger corrections could consequently be required, which then have an increasing effect on the image quality. In order to avoid this, in one embodiment of the invention, a measure for varying the at least one reconstruction parameter, preferably with an indication about a direction, an amount and/or a type of variation, i.e. a measure for the performed correction of the position of the oral cavity is displayed together with the 2D panoramic image. The user thus receives feedback about how good the position of the oral cavity within the used apparatus was.

In another embodiment, the image regions that have been subjected to a correction, for example due to a change in the position during the acquisition of the projection images, are marked or highlighted in the displayed 2D panoramic image itself. Such highlighting can be effected, for example, with a coloration of the corresponding image regions. The marking can also show the measure of the performed correction. A red coloration, for example, could represent regions, in which the necessary correction is so large that the desired image quality is no longer achieved, while a yellow coloration could represent regions, in which a correction has been performed, but the image quality is still acceptable.

It goes without saying that, if the image calculated in Steps F) or K) is already a 2D panoramic image, the derivation of the 2D panoramic image in Step G) is a trivial operation that does not require any further calculation. However, if the image calculated in Steps F) or K) is a 3D image, for example, the 2D panoramic image has to be calculated from said 3D image in Step G).

In one embodiment, outputting the 2D panoramic image in Step H) includes the delivery of a data set describing the 2D panoramic image, for example to a display or a further data processing device.

The above-described embodiments of the method according to the invention can at least partially be realized by using a software-controlled data processing device, i.e. a computer. It is therefore obvious that a computer program, which provides such software control for execution on the computer, and a storage medium, on which such a computer program is stored, are to be considered aspects of the invention.

At least one of the aforementioned objects is also achieved with an apparatus for producing a 2D panoramic image of an oral cavity, comprising a recording unit having a radiation source and an electronic image sensor, wherein the recording unit is configured and designed such that a plurality of projection images can be acquired during an at least partial revolution of the recording unit about the oral cavity in a given position, and a computer, wherein the computer is operatively connected to the image sensor such that said computer receives the plurality of projection images from the image sensor, and wherein the computer is configured such that the computer executes the steps A) receiving the plurality of projection images from the recording unit, B) calculation of an image including at least one anatomical feature from the plurality of projection images using a calculation rule with reconstruction parameters, C) provision of a model of the at least one anatomical feature, which describes the at least one anatomical feature in a target position in an image, D) identification of the at least one anatomical feature in the calculated image.

E) determination of a deviation between an actual position of the at least one identified anatomical feature in the calculated image and the target position of the at least one anatomical feature in the model by applying a metric, F) variation of at least one of the reconstruction parameters and recalculation of at least one part of the image that shows the at least one anatomical feature using the calculation rule and the at least partially varied reconstruction parameters or variation of a pixel transformation and application of the pixel transformation to at least one part of the calculated image that shows the at least one anatomical feature, so that at least this part of the image is recalculated, G) derivation of the 2D panoramic image from the recalculated image; and H) outputting the 2D panoramic image.

To the extent that aspects of the invention have previously been described with respect to the method, said aspects also apply to the corresponding apparatus for producing a 2D panoramic image of an oral cavity. Insofar as the method is carried out with an apparatus according to this invention, said apparatus comprises the appropriate devices for this purpose.

BRIEF DESCRIPTION OF THE DRAWINGS

Further advantages, features and possible applications of the present invention will become apparent with the aid of the following discussion of embodiments as well as the associated figures.

DETAILED DESCRIPTION

Identical elements in the figures are labeled with identical reference signs.

Figure 1:
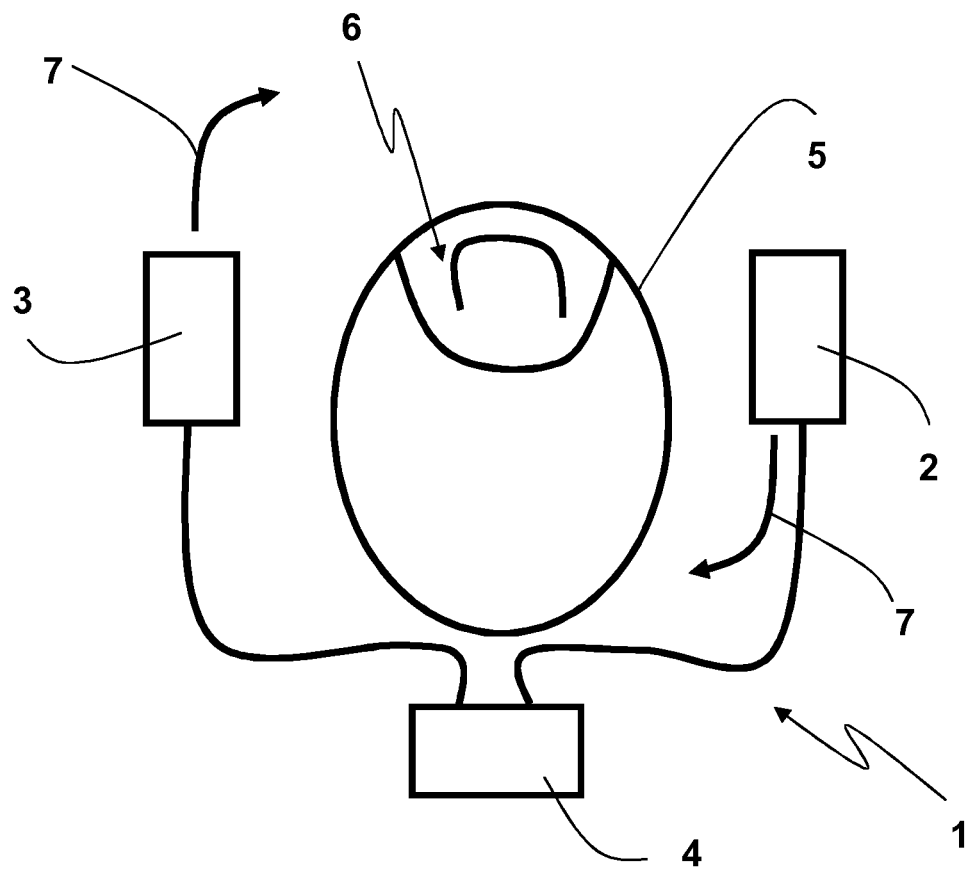
FIG. 1 is a horizontal schematic sectional view of an apparatus for producing a 2D panoramic image according to one embodiment of the present invention.
Figure 2:
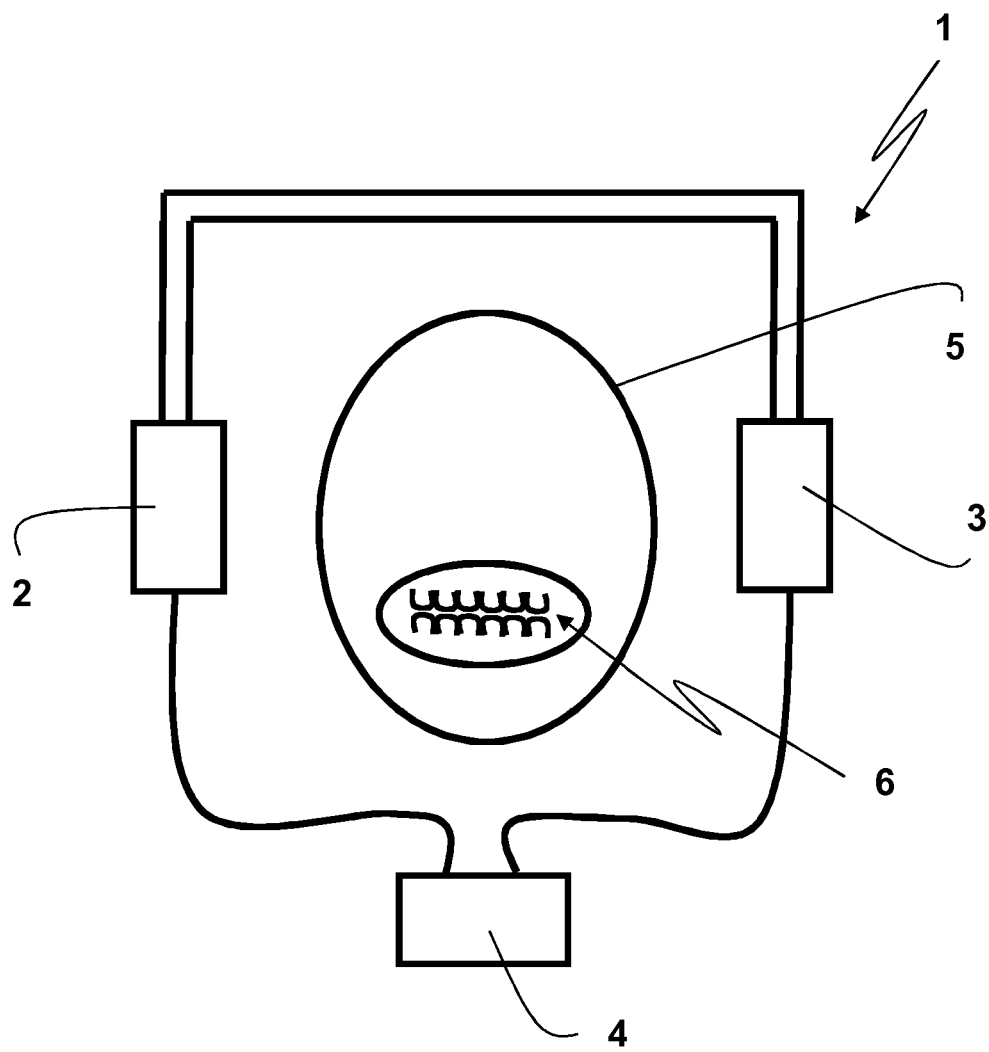
FIG. 2 is a schematic front view of the apparatus of FIG. 1.

FIG. 1 shows a schematic horizontal sectional view of an apparatus 1 according to the invention for producing a 2D panoramic image. FIG. 2 shows the same apparatus 1 in a view from the front. The apparatus 1 substantially comprises a source 2 for X-ray radiation and an electronic image sensor 3 for said X-ray radiation. In the context of the present invention, the source 2 and the image sensor 3 together form the recording unit. The sensor 3 is connected via corresponding data interfaces to a computer 4, which calculates a 2D panoramic image from the projection images acquired by the sensor 3.

During the recording of the head 5 of the patient, i.e. his oral cavity 6, the source 2 and the sensor 3 undergo a revolution along a predefined curved path. The source 2 and the sensor 3 are thereby respectively located on opposite sides of the head 5, so that the X-ray radiation from the source 2 to the sensor 3 is transmitted through the head 5. The sensor 3 detects the X-ray radiation transmitted by the head 5 from the source 2 from a plurality of angular positions along the revolution path 7, so that, after the revolution, a plurality of projection images are available to the computer 4 as raw data for the calculation of the 2D X-ray panoramic layer image. In the context of the present application, the depicted arrangement of source 2, sensor 3 and oral cavity 6, as well as the predetermined revolution path 7, determine the recording geometry.

Figure 3:
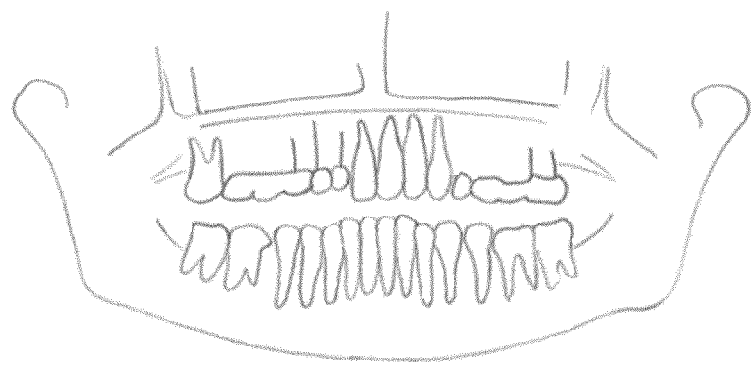
FIGS. 3a) to 3c) are schematic illustrations of 2D X-ray panoramic images for different positions of the oral cavity of the patient.
Figure 3:
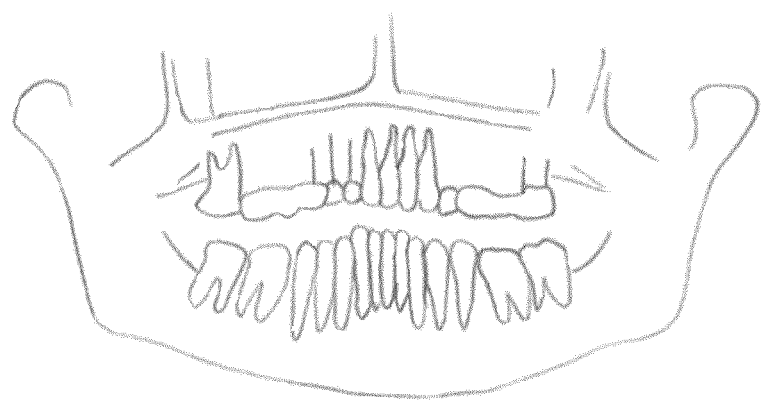
Figure 3:
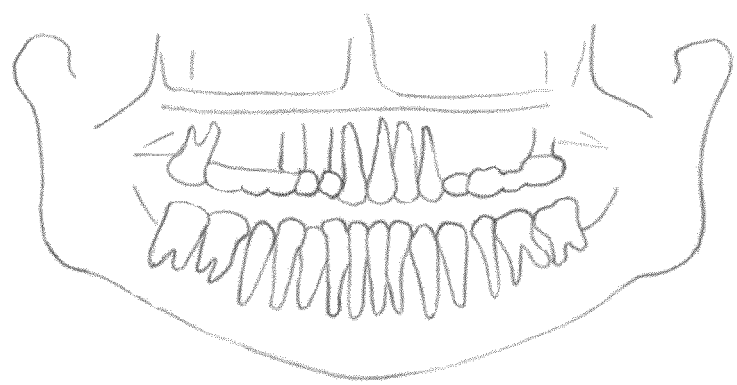

FIGS. 3a) to 3c) schematically show three 2D panoramic X-ray layer images, from which can be seen the dependence of the image of the oral cavity 6 and its elements in the panoramic image from the position of the head 5 relative to the source 2 and the sensor 3 during the acquisition of the plurality of projection images.

FIG. 3a) shows the panoramic image, wherein both the head inclination, i.e. orientation, and the head position, i.e. the location of the head, deviate from the optimum position. The panoramic image of FIG. 3b), on the other hand, is based on an optimum head position, wherein the head is, however, still inclined. In the panoramic image of FIG. 3c), both the head position and the head inclination are optimized.

The object of the present invention is now to obtain an optimized panoramic layer image which, as in the example of FIG. 3c), shows the jaw bone and teeth for an optimized head position and head inclination. However, this is independent of the actual head inclination and head position, i.e. the given position of the head during the generation of the projection images using the source 2 and the sensor 3, and thus of the recording geometry.

The deviation of the actual position in a first calculated 2D panoramic image from the optimum position, i.e. a target position, must consequently be determined, and a corrected 2D panoramic image must then be calculated by varying at least one reconstruction parameter in the calculation rule. The corrected 2D panoramic image should ultimately look like a good approximation of the illustration of FIG. 3c).

Figure 4:
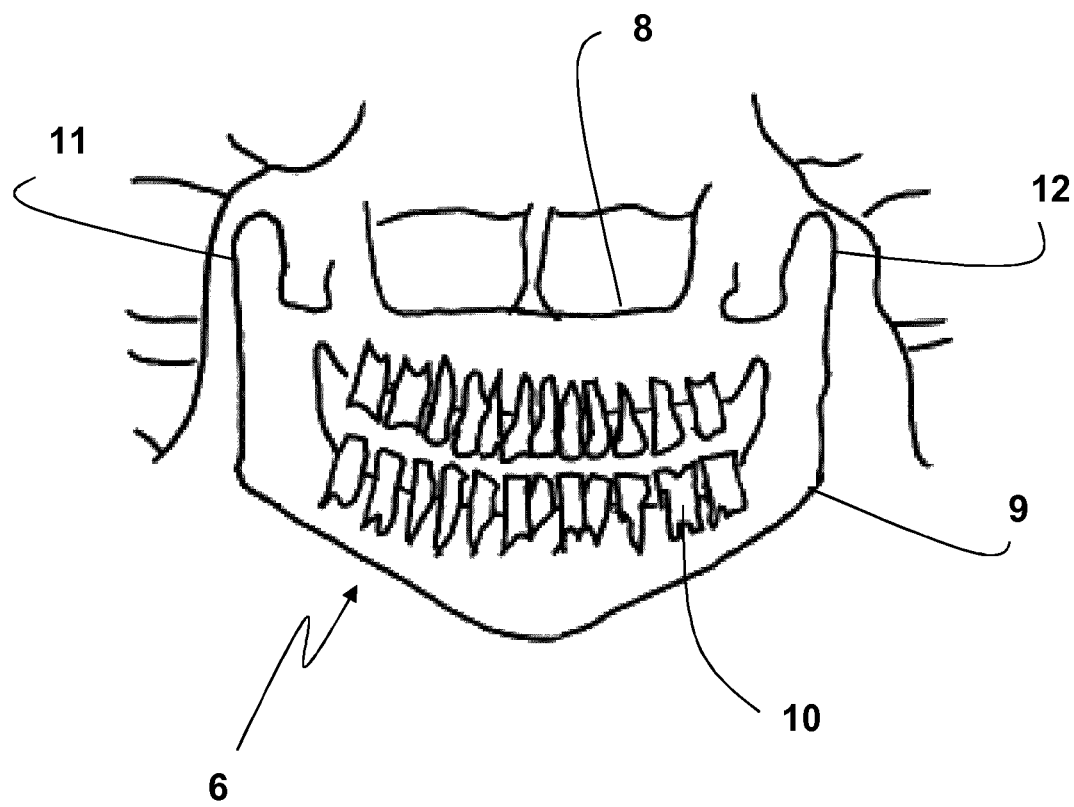
FIG. 4 is a schematic illustration of a 2D X-ray panoramic image of an oral cavity comprising a series of anatomical features.

In their presentation in an image, in particular in a 2D panoramic image, specific anatomical features of the head 5 can allow inferences to be drawn about the given position of the head 5 during the acquisition of the plurality of projection images, as well as about the depicted actual position of the head or oral cavity in a calculated image. FIG. 4 schematically shows a panoramic image of an oral cavity, wherein the oral cavity 6 is positioned optimally with respect to head inclination and head position. Possible features, which can be used to determine a deviation between said optimum target position and the actual position during the acquisition of the projection images, are the shape and the symmetry of the soft palate 8, the tooth and bone profile of the jaw bones 9 and the teeth 10 as well as the arrangement and the symmetry of the temporomandibular joints 11, 12.

A model can now describe the shape and the symmetry of one or more of these anatomical features 8, 9, 10, 11, 12 in the presentation of an optimum image, in particular an optimum 2D panoramic image. This model defines the target position of the selected anatomical feature and thus of the oral cavity 6. Since the model has to contain only a simplified presentation of one or more anatomical features rather than a complete 2D panoramic image of the oral cavity 6, this model comprises a significantly smaller quantity of data than a complete 2D panoramic image. This reduces the time required for determining deviations between the calculated image and the model.

In order to identify a mispositioning, i.e. a deviation of the given position of the head 5 during the acquisition of the plurality of projection images from the target position, when calculating the 2D panoramic image, the first calculated 2D panoramic image is compared with the model, and at least one reconstruction parameter is then varied until the anatomical feature in the calculated 2D panoramic image largely corresponds to the shape and position of said feature as described in the model.

Figure 5:
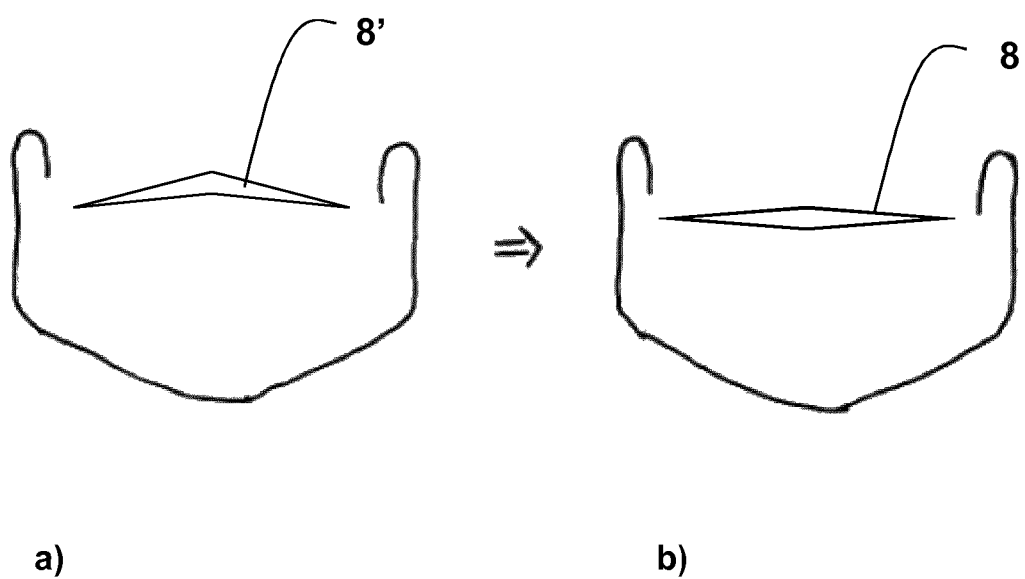
FIG. 5a) is a schematic Illustration of the soft palate of FIG. 4 in a 2D X-ray panoramic image when the patient's head is dorsally inclined.
FIG. 5b) is a schematic illustration of the 2D X-ray panoramic image of the soft palate with a corrected head inclination.

An example of this for the soft palate 8 is shown in Figures 5a) and b). After the first calculation of the 2D panoramic image from the plurality of projection images, the soft palate 8' looks like a slightly tilted gabled roof in the presentation of Figure 5a). A comparison with the model shows that the given position during the acquisition of the plurality of projection images was a dorsal inclination of the head. The reconstruction parameters responsible for the actual position in the calculated image are varied and the 2D panoramic image is then recalculated. This iteration is carried out until the deviation between the model and the presentation of the soft palate 8 in the 2D panoramic image is less than a predetermined threshold value. Therefore, in an idealized view, FIG. 5b) shows both the presentation of the soft palate 8 in the model and the presentation of the soft palate 8 in the corrected 2D panoramic image, from which the mispositioning of the head 5 during the acquisition of the plurality of projection images has been removed.

Figure 6:
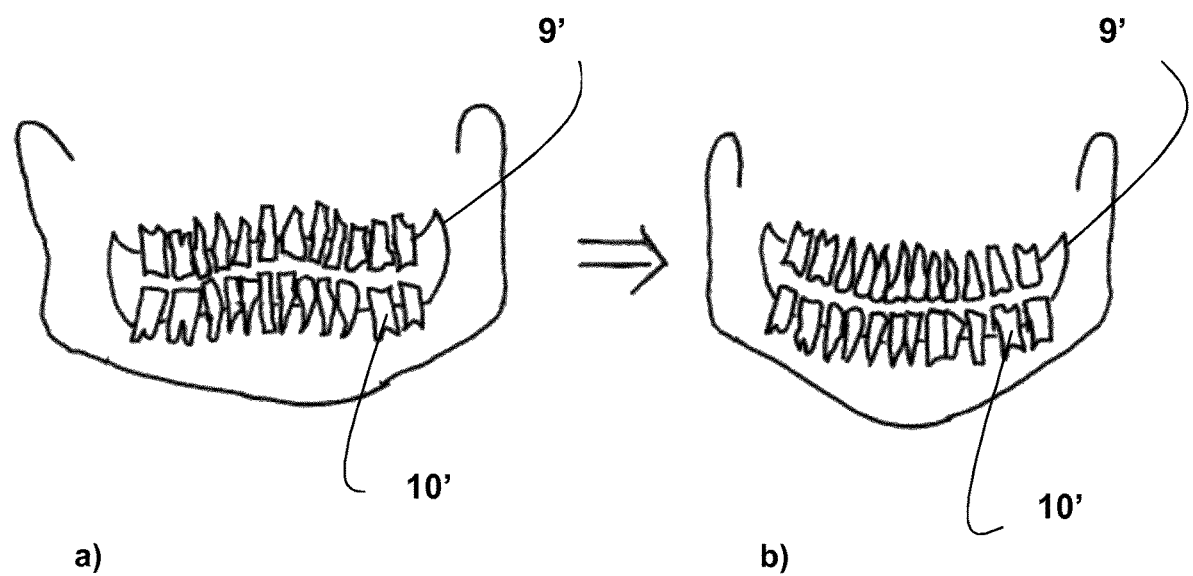
FIG. 6a) is a schematic illustration of the tooth and bone profile of the upper and lower jaw in a 2D X-ray panoramic image when the patient's head is dorsally inclined.
FIG. 6b) is a schematic illustration of the 2D X-ray panoramic image of the tooth and bone profile of FIG. 6a) with a corrected head inclination.

FIGS. 6a) and b) show a corresponding correction based on a model, which uses the profile of the jaw bone 9 and the teeth as an anatomical feature for the correction. After the calculation of the 2D panoramic image, the upper jaw bone 9' and the teeth 10' accommodated therein show a concave profile. On the other hand, the profile of the lower jaw bone and the teeth accommodated therein is convex. A comparison with the model shows that, here too, the head was dorsally inclined during the acquisition of the plurality of projection images. The reconstruction parameters responsible for the position are varied and the 2D panoramic image is then recalculated. This iteration is carried out until the deviation between the model and the presentation of the profile of jaw bone and teeth in the 2D panoramic image is minimal. Therefore, in an idealized view, FIG. 6b) shows both the tooth and bone profile of the model and the tooth and bone profile in the corrected 2D panoramic image, from which the mispositioning of the head 5 during the acquisition of the plurality of projection images has been removed.

Figure 7:
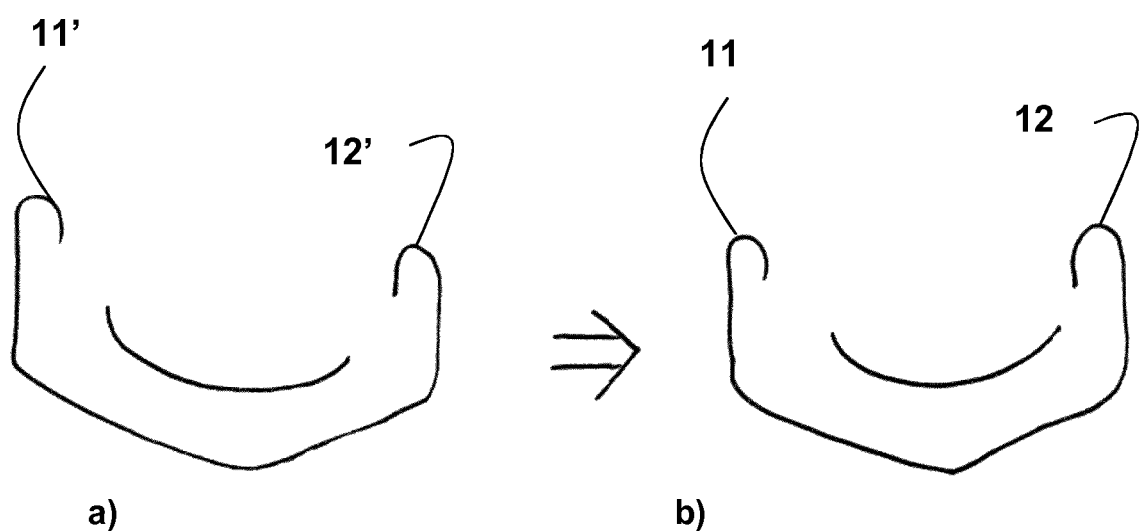
FIG. 7a) is a schematic illustration of a 2D X-ray panoramic image of the temporomandibular joints when the head is laterally inclined.
FIG. 7b) is a schematic illustration of a 2D X-ray panoramic image of the temporomandibular joints with a corrected head inclination.

FIGS. 7a) and b) show a correction based on a model, which uses the position and symmetry of the temporomandibular joints 11, 12 as an anatomical feature for the correction. In the case of the dorsal inclination of the head of FIG. 7a), the temporomandibular joints 11, 12 appear at different heights. The overall arrangement is therefore asymmetrical. In the corrected 2D panoramic image of FIG. 7b) on the other hand, which corresponds to the model in an idealized manner, the position of the temporomandibular joints 11, 12 is symmetrical.

LIST OF REFERENCE SIGNS 1 apparatus
2 source
3 sensor
4 computer
head
6 oral cavity
7 revolution path
8 soft palate
9 jaw bone
10 teeth
11, 12 temporomandibular joints

The invention claimed is:

1. Method for generating a 2D panoramic image of an oral cavity comprising the steps
   A) Provision of a plurality of projection images acquired during an at least partial revolution of a recording unit comprising a radiation source and an electronic image sensor about the oral cavity in a given position,
   B) Calculation of an image including at least one anatomical feature from the plurality of projection images using a calculation rule with reconstruction parameters,
   C) Provision of a model of the at least one anatomical feature, which describes the at least one anatomical feature in a target position in an image,
   D) Identification of the at least one anatomical feature in the calculated image,
   E) Determination of a deviation between an actual position of the at least one identified anatomical feature in the calculated image and the target position of the at least one anatomical feature in the model by applying a metric,
F) Variation of at least one of the reconstruction parameters and recalculation of at least one part of the image that shows the at least one anatomical feature using the calculation rule and the at least partially varied reconstruction parameters or variation of a pixel transformation and application of the pixel transformation to at least one part of the calculated image that shows the at least one anatomical feature, so that at least this part of the image is recalculated,
F-1) Redetermination of the deviation between the actual position of the at least one identified anatomical feature in the calculated image and the target position of the at least one anatomical feature in the model by applying a metric,
G) Derivation of the 2D panoramic image frons the recalculated image; and
H) Outputting the 2D panoramic image.

2. Method according to claim 1, wherein after Step F-1) and before Step G) the method comprises the following steps:
F-2) Repetition of Steps F) and F-1) until the determined deviation is less than a specified threshold value and
F-3) if the entire image was not recalculated in Step F-1), recalculation of at least one part of the image that was not yet recalculated in Step F) using the at least partially varied reconstruction parameters or applying the at least one pixel transformation to at least one part of the image that was not yet recalculated in Step F).

3. Method according to claim 1, wherein the provision of the plurality of projection images in step A) includes an acquisition of the plurality of projection images during an at least partial revolution of the recording unit about the oral cavity.

4. Method according to claim 1, wherein the calculation rule is designed such that the variation of the at least one reconstruction parameter in Step F) leaves at least one further imaging property, different from the position of the oral cavity, of the 2D panoramic image displayed in Step H) substantially unchanged.

5. Method according to claim 4, wherein, when varying the at least one reconstruction parameter, an effect of said at least one reconstruction parameter on the at least one further imaging property is substantially compensated in Step F).

6. Method according to claim 4, wherein the at least one further imaging property of the 2D panoramic image displayed in step H) is selected from a position of a layer that is sharply imaged in the 2D panoramic image, a radiation penetration angle and a thickness of the imaged layer.

7. Method according to claim 1, wherein a plurality of reconstruction parameters are varied in Step F), sc that, in addition to the position of the oral cavity, a further imaging property different from the position of the oral cavity changes, wherein the calculation rule is designed such that the position of the oral cavity and the further imaging property are changed independently of one another.

8. Method according to claim 1, wherein the at least one anatomical feature is selected from a position and or shape of a tooth, a temporomandibular joint, a palate, at least one element of the spine, a collarbone and/or a bone.

9. Method according to claim 1, wherein the at least one anatomical feature comprises anatomical symmetry.

10. Method according to claim 1, wherein the model describes the anatomical feature in the form of a 2D description or a 3D description.

11. Method according to claim 1, wherein:
in Step D), at least one anatomical feature is identified in a first section and at least one anatomical feature is identified in a second section of the calculated image,
in Step E), deviation between the at least one anatomical feature identified in the first section and the model, and a deviation between the at least one anatomical feature identified in the second section and the model, are determined by applying a metric,
in Step F), at least one reconstruction parameter for the first section and at least one reconstruction parameter for the second section of the calculated image are varied separately from one another,
in Step F-1), a deviation between the at least one identified anatomical feature in the first section and the model, and a deviation between the at least one identified anatomical feature in the second section and the model, are again determined by applying a metric, and
in Step J), Steps F) and F-1) are repeated until the respective determined deviations are less than a specified threshold value.

12. Method according to claim 11, wherein the first section of the calculated image is an upper section, which includes at least parts of the upper jaw, and the second section of the calculated image is a lower section, which includes at least parts of the lower jaw.

13. Method according to claim 1, wherein the method for collecting a change in the position of the oral cavity is used during a revolution of the recording unit, wherein the first section and the second section of the calculated image are arranged directly or indirectly adjacent to one another in a revolution direction of the recording unit.

14. An Method according to claim 1, wherein a measure for the variation of the at least one reconstruction parameter, preferably with a specification of a direction, an amount and/or a type of variation is provided along with the 2D panoramic image in Step H).

15. Apparatus for generating a 2D panoramic image of an oral cavity comprising:
a recording unit having a radiation source and an electronic image sensor,
wherein the recording unit is configured and designed such that a plurality of projection images can be acquired during an at least partial revolution of the recording unit about the oral cavity in a given position,
and a computer,
wherein the computer is operatively connected to the image sensor such that
said computer receives the plurality of projection images from the image sensor, and
wherein the computer is configured such that the computer executes the steps
A) Receiving the plurality of projection images from the recording unit,
B) Calculation of an image including at least one anatomical feature from the plurality of projection images using a calculation rule with reconstruction parameters,
C) Provision of a model of the at least one anatomical feature, which describes the at least one anatomical feature in a target position in an image,
D) Identification of the at least one anatomical feature in the calculated image,
E) Determination of a deviation between an actual position of the at least one identified anatomical feature in the calculated image and the target position of the at least one anatomical feature in the model by applying a metric,
F) Variation of at least one of the reconstruction parameters and recalculation of at least one part of the image that shows the at least one anatomical feature using the calculation rule and the at least partially varied reconstruction parameters or Variation of a pixel transformation and application of the pixel transformation to at least one part of the calculated image that shows the at least one anatomical feature, so that at least this part of the image is recalculated, F-1) Redetermination of the deviation between the actual position of the at least one identified anatomical feature in the calculated image and the target position of the at least one anatomical feature in the model by applying a metric, G) Derivation of the 2D panoramic image from the recalculated image; and H) Outputting the 2D panoramic image.

* * * * *